United States Patent
Wuts

(10) Patent No.: US 7,196,208 B2
(45) Date of Patent: Mar. 27, 2007

(54) PROCESSES FOR PREPARING 7-CARBOXY SUBSTITUTED STEROIDS

(76) Inventor: Peter Guillaume Marie Wuts, 8835 Pine Island Ct., N. Mattawan, MI (US) 49071

(*) Notice: Subject to any disclaimer, the term of this patent is extended or adjusted under 35 U.S.C. 154(b) by 423 days.

(21) Appl. No.: 10/392,956

(22) Filed: Mar. 21, 2003

(65) Prior Publication Data

US 2004/0087562 A1  May 6, 2004

Related U.S. Application Data

(60) Provisional application No. 60/424,102, filed on Nov. 6, 2002.

(51) Int. Cl.
*C07D 307/94* (2006.01)
(52) U.S. Cl. ...................... 549/265; 549/330
(58) Field of Classification Search ............. 549/265, 549/330
See application file for complete search history.

(56) References Cited

U.S. PATENT DOCUMENTS

| | | | |
|---|---|---|---|
| 3,787,396 A | 1/1974 | Weier | 260/239.57 |
| 4,069,219 A * | 1/1978 | Weier | 540/44 |
| 4,559,332 A | 12/1985 | Grob et al. | 514/175 |
| 5,237,064 A | 8/1993 | Bakshi et al. | 546/14 |
| 5,981,744 A | 11/1999 | Ng et al. | 540/41 |

FOREIGN PATENT DOCUMENTS

WO   WO 98/25948   6/1998

OTHER PUBLICATIONS

Ali, H. et al., *J. Med. Chem.* (1993), 36(21), 3061-3072.
Martin, J.C., et. al., *J. Amer. Chem. Soc.*, (1991), 113, 7277-7287.
Murahashi, Shun-ichi, "Palladium (o)-Catalyzed Carbonylation of Allyl Phosphates and Allyl-Acetates. Selective Synthesis of beta, gamma-Unsaturated Esters" *Tetrahedron Letters*, vol. 29, No. 39, 1988, 4945-4948.
Page, P. C., *Tetrahedron* (1991), 47, 2871-2878.
Panda, J., et. al., *Tetrahedron Letters* (1999), 40, 6693-6694.
Paquette, L. A., et. al., *J. Am. Chem. Soc.* (1995), 117(4), 1455-6.
Pollack, et. al., *J. Amer. Chem. Soc.*, 1987, 109, 5048-5050.
Rehnberg, N., et. al., *J. Org. Chem.* (1990), 55(14), 4340-9.
Schwede, W. et. Al., *Steroids* (1998), 63(3), 166-177.
Tomioka, K., et. al., *J. Org. Chem.* (1988), 53(17), 4094-4098.
Tsubuki, et. al., *J. Org. Chem.*, 1992, 57, 2930-2934.
Turuta, A. M. et. Al., *Mendeleev Commun.* (1992), 47-8.
Uchiyama, M., et. al., *Tetrahedron Letters* (2000), 41(51), 10013-10017.

Vanderiei, J. M. de L., *Synthetic Communications* (1998), 28(16), 3047-3055.
Waldemar, A., et. al., *Chem. Rev.*, (2001), 101, 3499-3548.
Zeng, et. al., *J. Amer. Chem. Soc.*, 1991, 113, 3838-3842.

\* cited by examiner

*Primary Examiner*—Amelia A. Owens
(74) *Attorney, Agent, or Firm*—Steven R. Eck; Charles W. Ashbrook

(57) ABSTRACT

This invention relates to processes for the preparation of 7-carboxy substituted steroid compounds of Formula I,

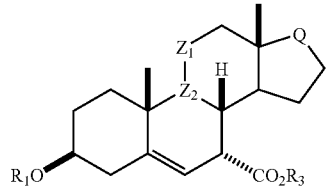

Formula I wherein $R_1$ is selected from H or $COR_4$;
$R_4$ is $C_1$–$C_6$ alkyl or $C_1$–$C_6$ alkoxy;
$R_3$ is $C_1$–$C_6$ alkyl;
$Z_1$ is —$CH_2$— or

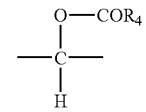

wherein O—$COR_4$ is in the α configuration;
$Z_2$ is —CH—;
or $Z_1$ and $Z_2$ may be taken together to form a carbon-carbon double bond;
Q is

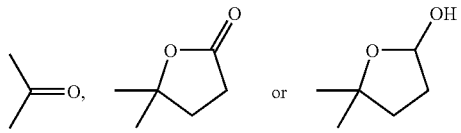

These intermediates are useful in the preparation of 7-carboxy substituted steroid compounds, and particularly, the invention is directed to novel and advantageous methods for the preparation of 9,11-α-epoxy-17-α-hydroxy-3-oxopregn-4-ene-α-7,21-dicarboxylic acid, γ-lactone, methyl ester (eplerenone; epoxymexrenone).

33 Claims, No Drawings

PROCESSES FOR PREPARING 7-CARBOXY SUBSTITUTED STEROIDS

CROSS-REFERENCE TO RELATED APPLICATION

This application claims the benefit of the following provisional application: U.S. Ser. No. 60/424,102, filed Nov. 6, 2002, under 35 USC 119(e)(i), which is incorporated herein by reference in its entirety.

BACKGROUND OF THE INVENTION

Certain 7-carboxy substituted steroids, for example eplerenone, are well known for their aldosterone antagonist activity and are thus useful in the treatment and prevention of diseases of the circulatory system. U.S. Pat. Nos. 4,559,332 and 5,981,744 and International Publication WO98/25948 describe a number of methods for the preparation of eplerenone and related compounds. However, the advent of new and expanded clinical uses for eplerenone create a need for improved processes for the manufacture of this and other related steroids. A major obstacle to the efficient synthesis of eplerenone and related steroid compounds is the introduction of a carboxy group at C-7. The current syntheses. involve the use of toxic cyanide reagents for the introduction of a C-7 carboxyl group.

SUMMARY OF THE INVENTION

This invention relates to processes for the preparation of 7-carboxy substituted steroid compounds of Formula I,

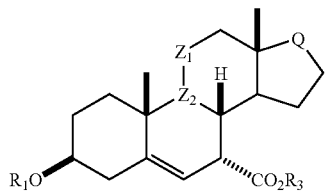

Formula I wherein $R_1$ is selected from H or $COR_4$;
$R_4$ is $C_1$–$C_6$ alkyl or $C_1$–$C_6$ alkoxy;
$R_3$ is $C_1$–$C_6$ alkyl;
$Z_1$ is —$CH_2$— or

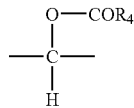

wherein O—$COR_4$ is in the α configuration;
$Z_2$ is —CH—;
or $Z_1$ and $Z_2$ may be taken together to form a carbon-carbon double bond;
Q is

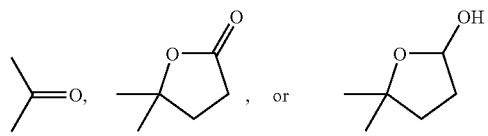

These intermediates are useful in the preparation of 7-carboxy substituted steroid compounds, and particularly, the invention is directed to novel and advantageous methods for the preparation of 9,11-α-epoxy-17-α-hydroxy-3-oxo-pregn-4-ene-α-7-21-dicarboxylic acid, γ-lactone, methyl ester (eplerenone; epoxymexrenone). A key step in the processes of this invention is reacting a steroid intermediate of Formula II,

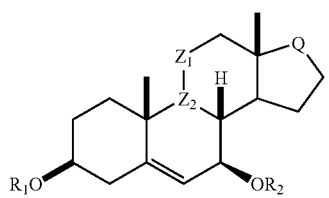

Formula II wherein $R_1$ and $R_2$ are independently H or $COR_4$;
$Z_1$, $Z_2$, $R_4$ and Q are as for Formula I;
with carbon monoxide in the presence of an alcohol, a base, and a palladium catalyst effectively inserting a carboxyl group at C-7, or "carbonylating" C-7, to provide the steroid compounds of Formula I.

Other intermediates of this invention are those of Formula IIIA;

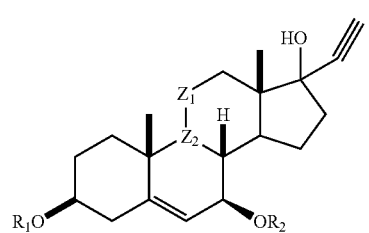

Formula IIIA wherein $R_1$, $R_2$, $Z_1$ and $Z_2$ are as for Formula II.

The novel synthesis schemes which take advantage of the 'cabonylating' reaction are described in detail in the Description of Embodiments.

DESCRIPTION OF THE EMBODIMENTS

Definitions

In the detailed description, the following definitions are used. The term "alkyl," by itself or as part of another substituent, means, unless otherwise stated, a straight or branched chain, or cyclic hydrocarbon radical, or combination thereof. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like.

The term "aryl," (Ar) employed alone or in combination with other terms (e.g., aryloxy, arylthioxy, aralkyl) means, unless otherwise stated, an aromatic substituent which can be a single ring or multiple rings (up to three rings), which are fused together or linked covalently.

Schematic Summary

Schemes I–IV provide schematic flow diagrams of examples of the processes of this invention.

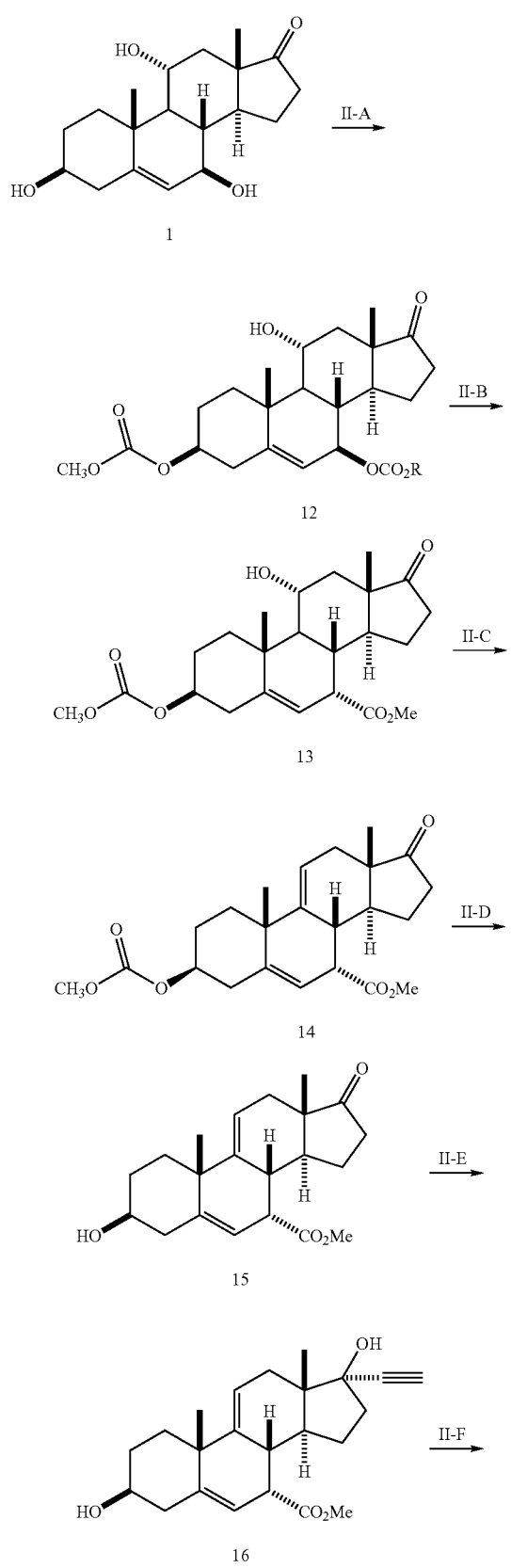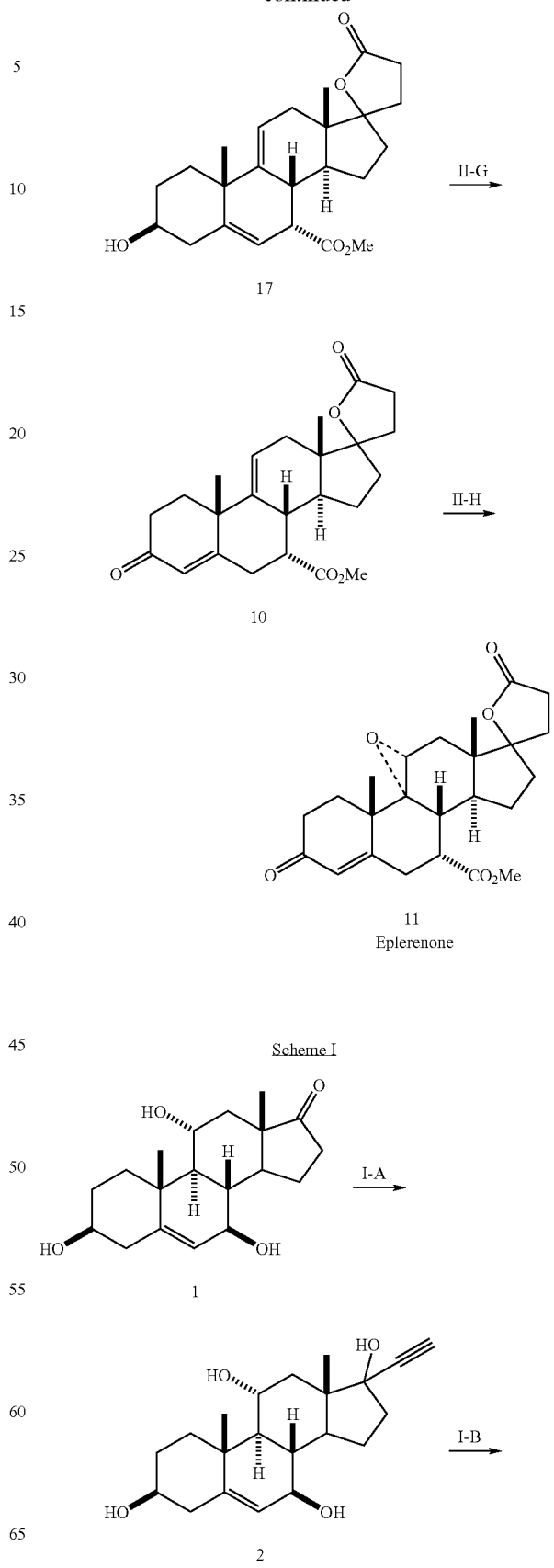

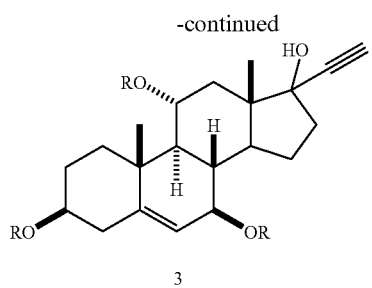
3
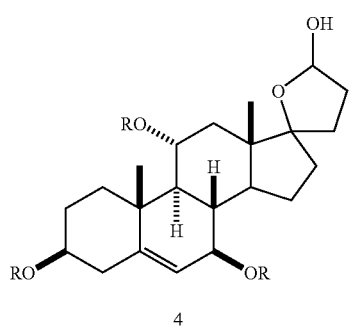
4
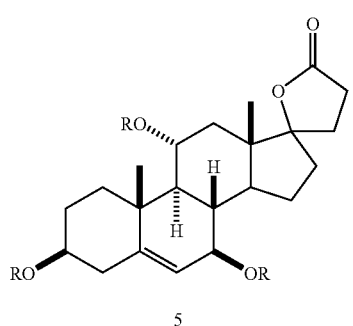
5
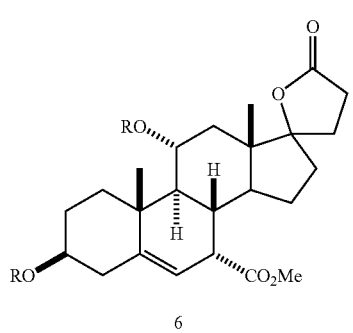
6
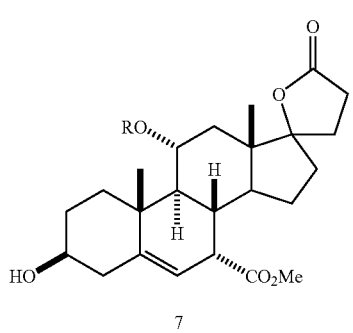
7
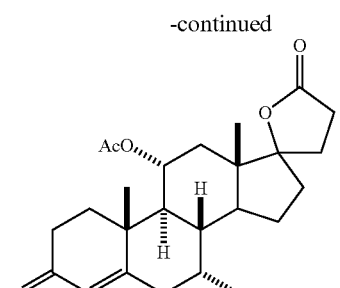
8
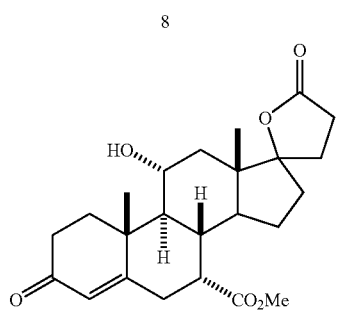
9
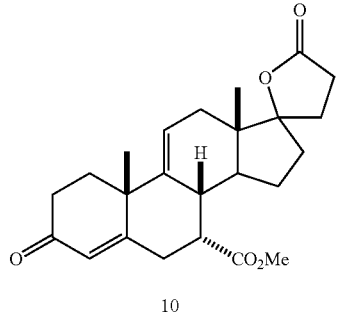
10
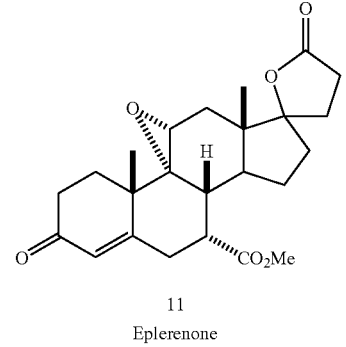
11
Eplerenone
Scheme III
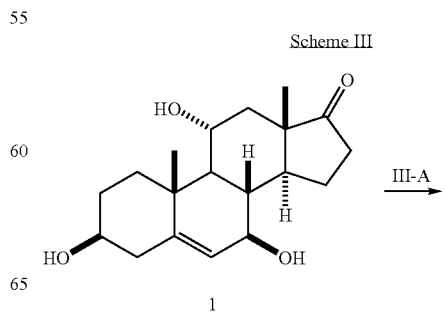
1

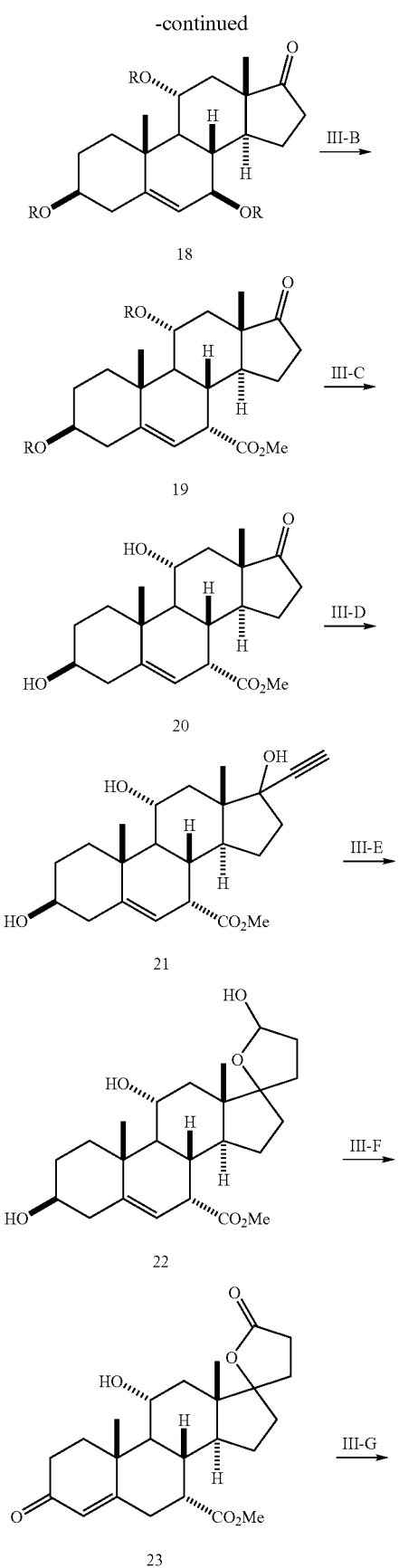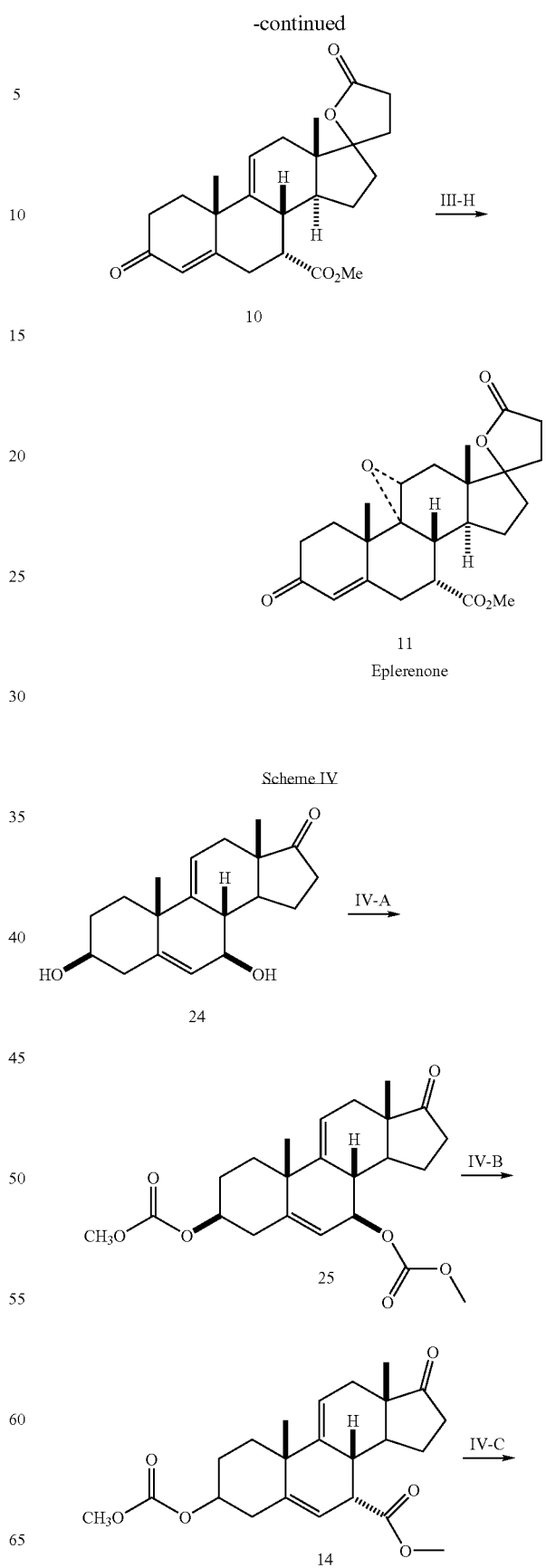

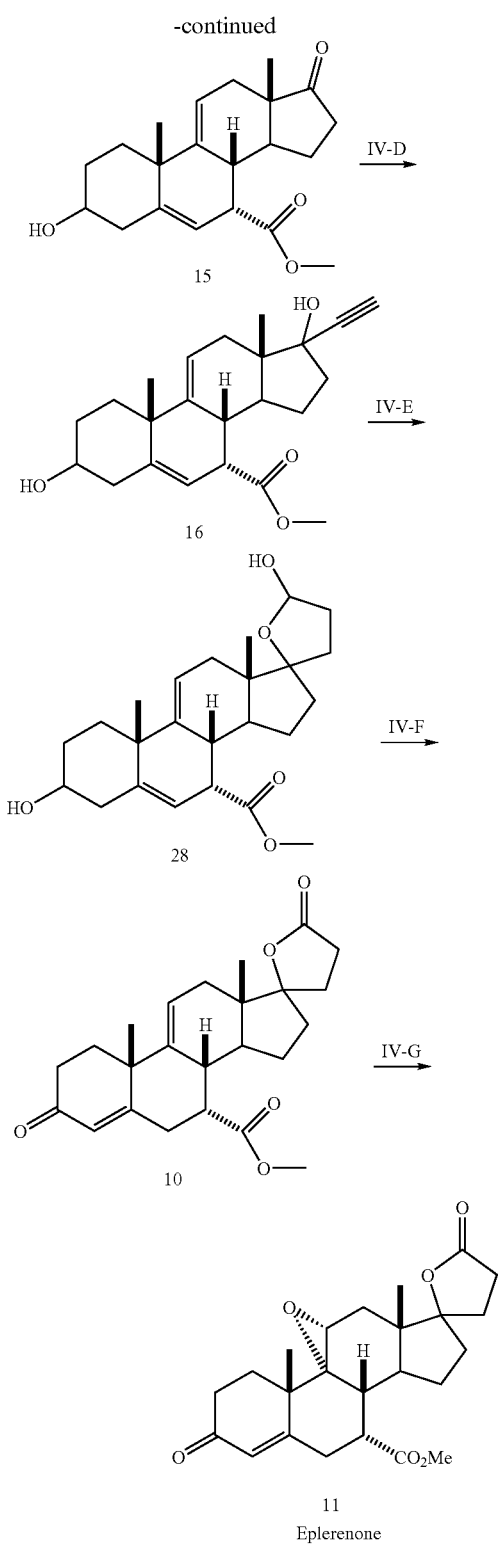

Preparation of the starting material 1, (3β,7β,11α-trihydroxy-5-androsten-17-one) for Schemes I–III may be obtained by the bioconversion of 5-androsten-3β-ol-17-one using a submerged culture of *Absidia coerulea* ATCC 6647 (synonym *Absidia orchidis*) at a 10-L fermentation scale. (See Example 17). The starting material for Scheme IV may be obtained by the bioconversion of 3β-hydroxyandrosta-5, 9(11)-dien-17-one (I) to 3β,7β-dihydroxyandrosta-5,9(11)-dien-17-one using a submerged culture of *Diplodia gossypina* ATCC 20571 (synonym *Botryodiplodia theobromae* IFO 6469) at a 10-L fermentation scale (see Example 16).

Steps I-A, II-E, III-D and IV-D: Addition of Acetylene to 17-oxo Intermediates 17-oxo intermediates are reacted with acetylene to provide the corresponding addition compounds according to procedures described in the literature (see for example: Schwede, W., et.al., Steroids, 63 166 (1998); Corey, E. J. et. al., J. Amer.Chem. Soc. (1999), 121, 710–714; Schwede, W. et.al., Steroids (1998), 63(3), 166–177; Ali, H. et.al., J. Med. Chem. (1993), 36(21), 3061; Turuta, A. M. et.al., Mendeleev Commun. (1992), 47–8; Kumar, V. et.al., Tetrahedron (1991), 47(28), 5099; Page, P. C., Tetrahedron (1991), 47, 2871–8; Curts, S. W. et.al., Steroids (1991), 56, 8; Kataoka, H. et.al., Chem. Lett. (1990), 1705–8; Christiansen, R. G. et.al., J. Med. Chem. (1990), 33(8), 2094–100). Optionally, the trihydroxy compound 1 in step I-A may be trimethylsilylated without isolation before the addition of acetylene. Silylation is achieved with hexamethyldisilazane and a mild acid catalyst such as trimethylsilyl chloride or saccharin. Following the addition of acetylene, the trimethylsilyl groups are removed during work-up of the reaction with mild mineral acid, acetic acid, phosphoric acid, tetra-alkylammonium fluoride and the like.

Steps I-B, II-A, III-A and IV-A: Hydroxy Acylations

Hydroxy intermediates are acylated with an acylating reagent in the presence of a tertiary organic base by procedures well known in the art. Acylating reagents include lower alkanoic anhydrides, lower alkanoic chlorides, lower alkylcarbonyl chlorides, lower alkylcarbonic anhydrides, and the like. Suitable tertiary organic bases include pyridine, 4-dimethyaminopyridine, 4-dimethyaminopyridine N-oxide, triethyl amine, diisopropylethyl amine and the like. Alternatively, preparation of mixed carbonates (RO—CO—O—) can be achieved by reaction with an alkoxycarbonyloxybenztriazole in the presence of a tertiary organic base according to published procedures (Harada, T., et.al., J. Carbohydrate Chem., (1995), 14, 165) with the modification that a polar solvent such as pyridine, dimethylformamide or acetonitrile is substituted for methylene chloride as the reaction solvent.

Steps I-C, II-F, III-E and IV-E: Hydroformylation of Acetylene Adducts

Formation of the lactol intermediates is achieved by hydroformylation with carbon monoxide and hydrogen in the presence of a catalytic amount of rhodium catalyst and a rhodium coordinating ligand according to procedures described in the literature (Wuts, P. G. M., et.al., J.Org.Chem. 1989, 54, 5180; Botteghi, C., et.al., Tetrahedron, 2001, 57, 1631). The reaction is conducted at a pressure between 14–500 psi, preferably between 100–200 psi. The ratio of hydrogen to carbon monoxide is 1/5 to 5/1, preferably 1/1. Suitable rhodium catalysts include rhodium acetate, rhodium chloride, hydridorhodiumtristriphenylphosphine and dicarbonyl acetylacetonato rhodium II. Suitable ligands include triarylphosphines, trialkyl phosphates, bidentate phosphines such as xantphos, bidentate phosphites and the like.

Steps I-D, II-G, III-F and IV-F. Oxidation of Lactols to Lactones:

Oxidation of lactols to lactones can be achieved with a variety of standard oxidizing reagents. Examples of suitable oxidizing reagents include: Iodosuccinimide/tetrabutyl ammonium iodide (Kraus, George A. Bioorganic & Medicinal Chemistry Letters (2000), 10(9), 895–897; Barrett, A. G. M., et.al., J. Org. Chem. (1989), 54(14), 3321); Jones reagent (chromic acid in acetone) (Panda, J., et.al., Tetrahedron Letters (1999), 40, 6693; Tomioka, K., et.al., J. Org. Chem. (1988), 53(17), 4094); Silver carbonate (Chow, T. J., et.al., J. Chem. Soc., Perkin Transactions 1, (1999), 1847); Pyridinium chlorochromate (Uchiyama, M., et.al., Tetrahedron Letters (2000), 41(51), 10013; Vanderiei, J. M. de L., Synthetic Communications (1998), 28(16), 3047; Kassou, M., et.al., Journal of Organic Chemistry (1997), 62, 3696; Rehnberg, N., et.al., J. Org. Chem. (1990), 55(14), 4340–9; RuO$_4$/tetralkylammonium salts/tert-amine N-oxide, Jeewoo, K., et.al., Chem. Lett. (1995), (4), 299; pyridinium dichromate, Paquette, L. A., et.al., J. Am. Chem. Soc. (1995), 117(4), 1455–6); sodium hypochlorite/tert-amine N-oxide (Waldemar, A., et.al., Chem. Rev., (2001), 101, 3499); aluminum alkoxides/acetone (Ooi, T., et.al., Synthesis (2002), 279; Djerassi,C. et.al., Org. React. (1951), 6, 207); triacetoxyperiodoindane (Martin, J. C., et.al., J.Amer.Chem.Soc., (1991), 113, 7277).

Steps I-E, II-B, III-B and IV-B: Carbonylation at C-7

Carbonylation of steroidal $\Delta^5$-ene-7-acylates (Formula 2) is accomplished by reaction with carbon monoxide in the presence of an alcohol, a base, such as an amine, a palladium catalyst, and optionally, a co-solvent to provide the steroid compounds of Formula I. In general, the palladium catalyst includes any ligated palladium complex, e.g., halide and/or organic ligands ligated to at least one Pd atom, which facilitates the conversion of the C-7 —OR$_2$ group in formula II to the desired —C(O)OR$_3$ group of formula I. Suitable palladium catalysts include, but are not limited to, palladium acetate, palladium (II) acetylacetonate, palladium (0)bis (dibenzylideneacetone) (Pd$_2$(dba)$_2$), palladium 1,3-diphenylphosphinopropane dibromide, (Pd(dppp)Br$_2$), dimethyl-2-(dimethylphosphino)ethylphosphine palladium and bistriphenylphosphine palladium dibromide (Pd$_2$(Ph$_3$P)$_2$ Br$_2$. Suitable bases include, but are not limited to N-methylmorpholine (NMM), triethylamine (TEA), diisopropylethylamine (DIPEA) and the like. Examples of the alcohol may include, but are not limited to, or benzyl alcohol or compounds of the formula $C_1$–$C_6$ alkyl-OH such as methanol, ethanol, 2-butanol, and isopropanol. Other examples of suitable alcohols may include any reactants containing an —OH functional group which together with the CO will form the desired ester at the steroid C-7 position. For instance, the alcohol may be any primary or secondary hydrocarbon reactant. Reactions may be conducted in an alcohol at temperatures between about 20° C. to about 150° C. and at pressures of CO between about 500 psi to about 2000 psi for about 5 to about 24 hours. For example, compounds of the invention may be produced using a temperature between 50° C.–90° C., e.g., 70–80° C., and CO pressures of 800–1500 psi, e.g., 1200–1400, in methanol for 10–12 hrs. The reaction mixture optionally contains bromide from for example lithium bromide. The results of carbonylation under a variety of conditions are summarized in Table 1. As can be seen, yields of product are dependent on conditions Specific conditions for this reaction are found in the examples.

TABLE 1

Carbonylation of C-7 Acyl Derivatives

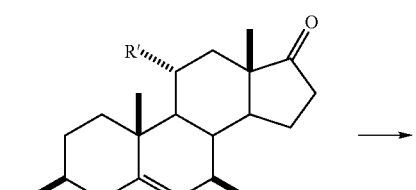

| Substrate | Palladium source/ligand | Base | Additive | Yield (%) |
|---|---|---|---|---|
| 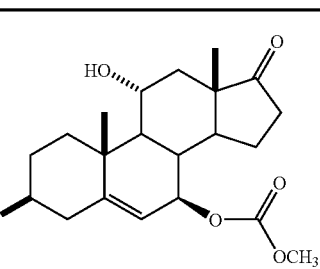 | Pd$_2$(dba)$_3$.CHCl$_3$ | NMM | PPh$_3$, NaBr, | 48 |

TABLE 1-continued

Carbonylation of C-7 Acyl Derivatives

| Substrate | Palladium source/ligand | Base | Additive | Yield (%) |
|---|---|---|---|---|
| (11α-OH, 3β-OC(O)OCH₃, 7β-OC(O)OCH₃ steroid) | Pd₂(dba)₃·CHCl₃ | NMM | PPh₃, NaBr | 60 |
| (11α-OH, 3β-OC(O)OCH₃, 7β-OC(O)OCH₃ steroid) | Br₂Pd(PPh₃)₂ | DIPEA | None | 80 |
| (11α-OAc, 3β-OAc, 7β-OAc steroid) | (dppe)PdBr₂ | DIPEA | LiBr, | 32 |
| (11α-OAc, 3β-OAc, 7β-OAc steroid) | (dppf)PdBr₂ | DIPEA | LiBr | <10 |

TABLE 1-continued

Carbonylation of C-7 Acyl Derivatives

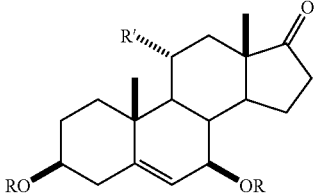

| Substrate | Palladium source/ligand | Base | Additive | Yield (%) |
|---|---|---|---|---|
| 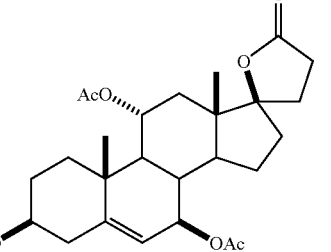 | (dppp)PdBr$_2$, | DIPEA, | LiBr, | 50 |
| 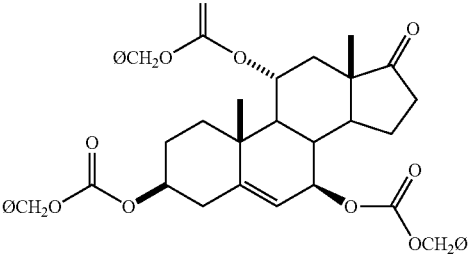 | Br$_2$Pd(PPh$_3$)$_2$ | DIPEA | None | <10 |
| | Pd(OAc)$_2$ | DIPEA | DMPE, | <10 |
| 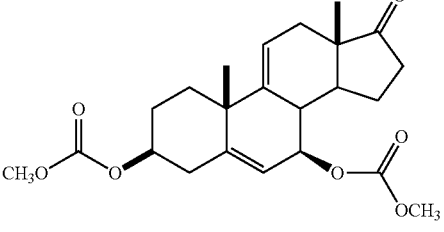 | Br$_2$Pd(PPh$_3$)$_2$ | DIPEA | NaBr, | 39 |

All reactions were conducted at 70–80° C. and 1200–1400 psi carbon monoxide in methanol for 10–12 hrs.

DMPE=Dimethyl-2-(dimethylphosphino)ethylphosphine; DIPEA=Diisopropylethylamine; NMM=N-methyl morpholine; IPA=Isopropyl alcohol; Pd(dppp)Br$_2$=bisdiphenylphosphinopropane palladium dibromide; Pd(dba)$_2$—CHCl$_3$=palladium(0)bis(dibenzylideneacetone)

Steps I-F, I-H, II-D, III-C, and IV-C: Acyl Group Hydrolysis

Hydrolysis of 3 and/or 11 acylhydroxy intermediates is accomplished with an alkaline earth hydroxide, bicarbonate or carbonate such as sodium hydroxide, potassium carbonate, sodium bicarbonate, cesium hydroxide, lithium bicarbonate and the like, using methanol as a solvent, optionally with a co-solvent. Carbonates may also be hydrolyzed using reagents such as trimethylsilyliodide or trimethylsilylbromide either with preformed reagents or with in-situ generated reagents in solvents such as acetontrile or methylene chloride.

Steps I-G, II-F, III-F and IV-F: Oxidation of 3-hydroxy-$\Delta^5$-ene Intermediates Oxidation of 3-hydroxy-$\Delta^5$ ene intermediates intermediate 7 to the $\Delta^4$-eneone 8 is achieved with reagents as described for Step I-C.

In those instances where the oxidation of Steps I-G, II-F, III-F and IV-F results in the unconjugated 5–6 double bond, migration of the double bond to the thermodynamically more stable $C_{4-5}$ position is accomplished by contacting intermediates such as 8 with an organic or inorganic acid in an inert organic solvent or an aqueous mixture of solvents at a temperature of from 0°–80° C. Suitable organic acids include, but are not limited to, toluenesulfonic acid, methanesulfonic acid, benzenesulfonic acid, trifluroacetic acid, oxalic, trichloroacetic acid and the like. Suitable inorganic acids include, but are not limited to, hydrochloric acid, hydrobromic acid, phosphoric acid, perchloric acid and the like. Alternatively, the catalyst can be a tertiary organic base such as triethylamine, diazabicycloundecane (DBU) and the like or an inorganic base such as sodium hydroxide, potassium hydroxide, calcium hydroxide and the like. The double bond migration has been described (Bakshi, et.al., U.S. Pat. No. 5,237,064; Pollack, et.al., J. Amer. Chem. Soc., 1987, 109, 5048; Tsubuki, et.al., J. Org. Chem., 1992, 57, 2930; Zeng, et.al., J. Amer. Chem. Soc., 1991, 113, 3838).

Step I-H

Hydrolysis of 8 is accomplished by procedures given in Step I-F

Steps I-I and I-J

Conversion of the known intermediate 9 to 10 (eplereneone) is described in U.S. Pat. Nos. 4,559,332, and 5,981,744.

EXAMPLES

Example 1

Addition of Acetylene to 17-oxo Intermediates

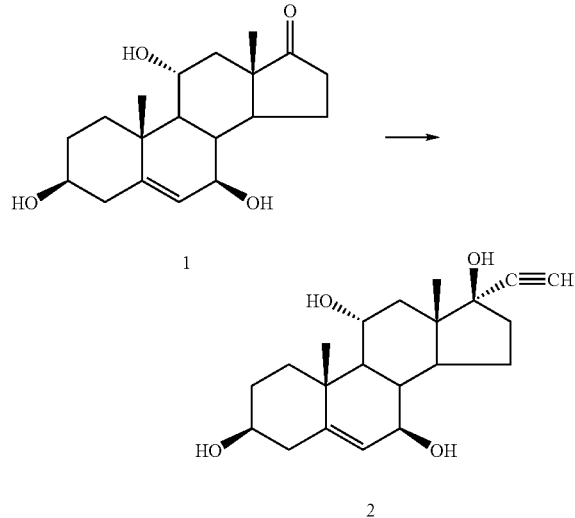

Hexamethyldisilazane (HMDS) (100 ml) is added to a stirred slurry of 50.0 g Triol 1 in 400 ml methylene chloride. Saccharin (0.57 g) is added and the mixture is heated under reflux for 3 hours during which time the slurry will gradually dissolve to a clear, amber solution. Water (5 ml) is added to quench any excess HMDS. After 5 minutes at reflux the mixture is filtered through a $CH_2Cl_2$ wet layer of 32.6 g magnesol on a 350 ml coarse frit filter funnel. The filtrate should be clear and almost colorless. The filter cake is washed with 2×100 ml $CH_2Cl_2$. The combined filtrates are concentrated under reduced pressure and residual methylene chloride is removed by evaporation with 2×500 ml portions of tetrahydrofuran (THF), concentrating to dryness after each addition to give a white solid A suspension of potassium t-butoxide (42.0 g) in 500 ml THF is cooled to −9°±5° C. with an ice/methanol bath. Acetylene is bubbled into the mixture just under the surface with moderate stirring at for at least 1 hour. The silylated steroid intermediate from above in THF (400 ml) is added over 30 min while maintaining a reaction temperature of 0°±5° C. After the addition, the mixture is stirred for a further hour at 5°±5° C. Water (100 ml) is added slowly allowing the reaction mixture to warm up to 15°±5° C. 125 ml of 10% HCl is slowly added to reduce the pH to 2.5 to 3. The mixture is stirred at pH 2.5 to 3, adding small amounts of 5% HCl as needed to maintain a pH of 2.5 to 3, for 1 to 2 hours at 20°±5° C. When the hydrolysis is complete, half saturated $NaHCO_3$ solution is added to raise the pH to 5.5 to 6. The mixture is diluted with ethyl acetate (500 ml) and the phases separated. The aqueous phase is extracted with ethyl acetate and the combined ethyl acetate phases are washed with water, brine, dried over magnesium sulfate and concentrated to give the addition product 2. $^{13}C$ NMR ($CDCl_3$) δ 141.99, 127.38, 89.37, 77.73, 75.24, 72.13, 70.54, 67.68, 54.13, 49.57, 47.43, 43.94, 42.58, 40.52, 40.22, 39.80, 39.59, 39.39, 39.01, 38.09, 31.95, 25.80, 18.58, 14.09.

Example 2

Hydroxy Acetylations

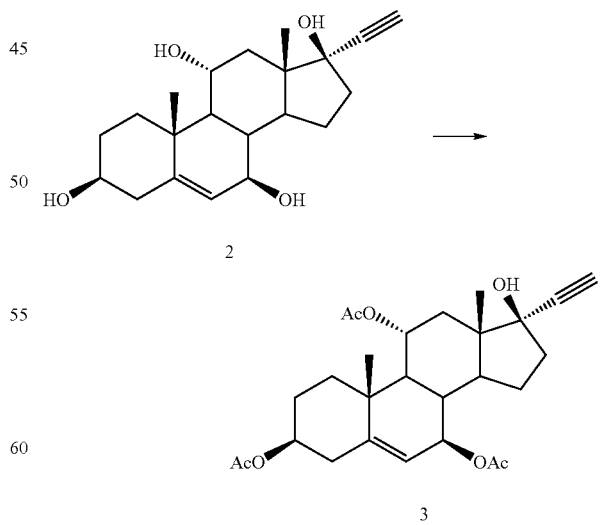

A mixture of the tetraol 2 (50.00 g, 144 mmol) dissolved in pyridine (150 ml) is cooled to <10° C. in an ice bath. Dimethylaminopyridine (DMAP) (1.7 g, 14 mmol) is added followed by slow addition of acetic anhydride (41.4 ml, 439 mmol) at a rate to maintain the solution temperature below 10° C. Following the addition, the reaction mixture is warmed to room temperature. The mixture is diluted with ethyl acetate (75 ml) and water (50 ml), stirred for 5 minutes and the layers separated. The organic layer is washed with 10% HCl (4×25 ml) followed by H₂O (2×50 ml), dried over MgSO₄ and concentrated. The product is recrystallized from toluene (100 ml).

$^{13}$C NMR (CDCl₃) δ 170.68, 170.10, 143.48, 128.90, 128.10, 125.17, 122.59, 86.63, 78.21, 75.07, 74.40, 72.79, 71.47, 50.16, 48.07, 47.02, 38.76, 38.06, 37.83, 37.67, 36.92, 27.66, 24.18, 21.74, 21.44, 18.65, 13.06.

Example 3

Hydroformylation of Acetylene Adducts

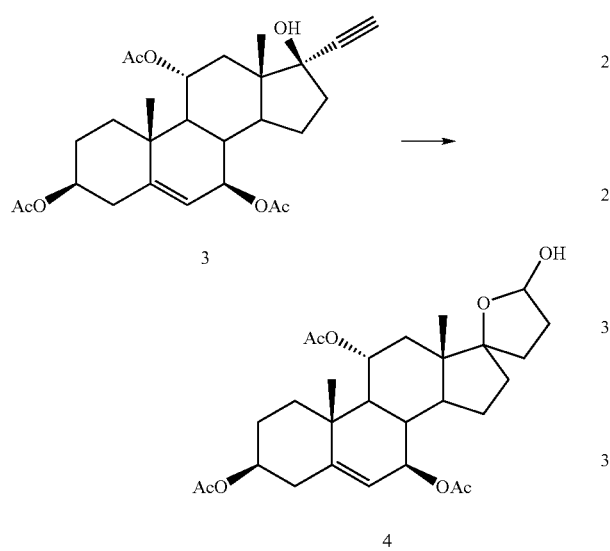

A solution of the triacetate 3 (25.4 g, 54 mmol), PPh₃ (2.13 g, 8.1 mmol) and Rh₂(OAc)₄ (716 mg, 1.62 mmol) in ethyl acetate (200 ml) is heated at 80° C. under a 1/1 mixture of hydrogen/carbon monoxide at a pressure of 170 psi for 12 hours. The mixture is concentrated under reduced pressure and the product 4 purified by column chromatography (70/30 EtOAc/Hex and 500 g silica). Typically the crude product was not characterized because of the lactol isomers resulted in poor quality NMR spectra. It was taken directly into the oxidation Example 4A Oxidation of Lactols to Lactones

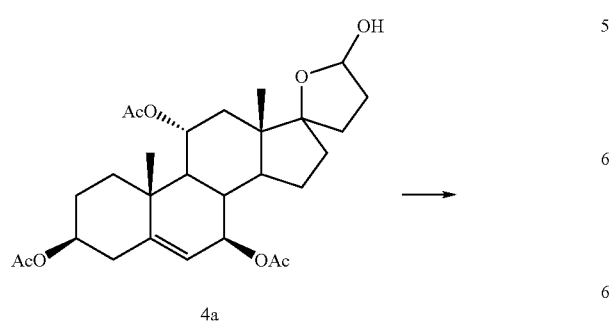

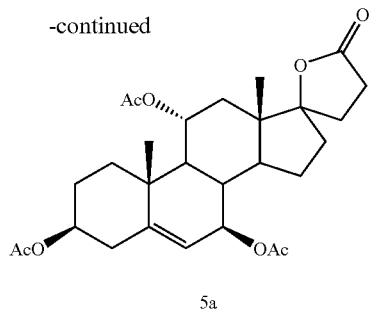

A mixture of the lactol 4a (25 g, 50 mmol), methylene chloride (250 ml), water (38 ml), 2,2,6,6-tetramethylpiperidin-1-oxyl (TEMPO) (156 mg, 1 mmol), KBr (595 mg, 5 mmol), and NaHCO₃ (5.5 g, 65 mmol) is cooled to ≦10° C. in an ice bath. A solution of 1.1 M sodium hypochlorite (NaOCl) (50 ml, 55 mmol) is slowly added. The mixture is allowed to warm to room temperature and diluted with water (50 ml). The layers are separated and the organic layer washed with brine (2×50 ml). The organic layer is dried with MgSO₄, filtered and concentrated to afford 5a as an off white foam. $^{13}$C NMR (CDCl₃) δ 177.94, 172.60, 172.15, 171.58, 145.49, 124.36, 96.18, (79.22, 78.90, 78.59 CDCl₃), 76.59, 74.57, 72.63, 52.14, 49.55, 47.75, 40.00, 39.75, 39.61, 38.65, 37.47, 32.74, 30.85, 29.56, 26.01, 23.61, 23.37, 23.17, 23.11, 20.52, 16.19.

Example 4B

Oxidation of Lactols to Lactones

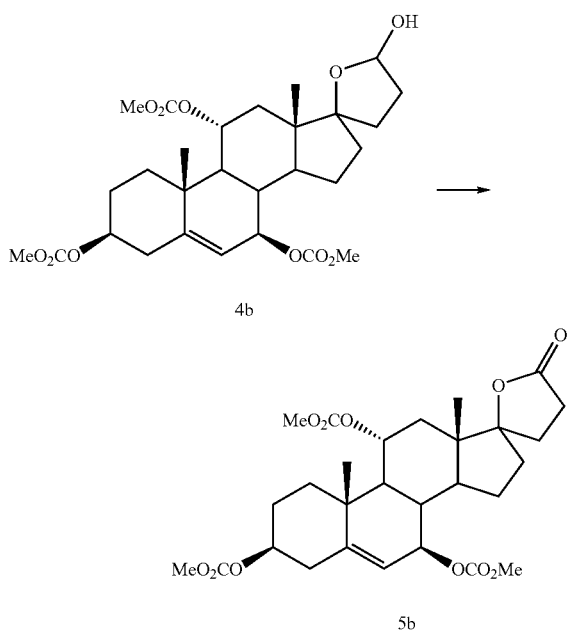

A solution of the lactol 4b (1.0 g) in 25 mL of CH₂Cl₂ and 9 mL of H₂O was treated with 300 mg of NaHCO₃, 142 mg of KBr, 15 mg of TEMPO and cooled to 5° C. NaOCl 2.4 mL was then slowly added. When the reaction was complete, the product was isolated with EtOAc and crystallized from EtOAc/Hex to give 876 mg of the lactone 5b. $^{1}$H NMR (CDCl₃) δ 5.39 (s, 1 H), 5.1 (m, 1 H), 4.98 (d, J=8.4 Hz, 1 H), 3.80 (s, 6 H), 3.78 (s, 3 H), 2.56–2.6 (m, H), 2.05–1.85 (m, H), 1.19 (s, 3 H), 1.04 (s, 3 H).

Example 5

Carbonylation at C-7

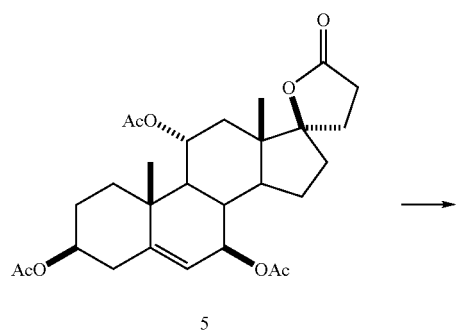

The triacetate 5 (2.0 g), Pd(dppp)Br$_2$ (126 mg), diisopropyl amine (0.78 mL), Et$_4$NBr (260 mg), NaBr (1.09 g) in 20 ml of methanol is pressurized to 1200 psi with CO then heated at 65° C. for twelve hours. The solution is cooled and concentrated and the residue chromatographed on silica gel with 40–75% ethyl acetate/hexane to give the methyl ester 6. $^{13}$C NMR (CDCl$_3$) δ 176.12, 172.77, 170.40, 169.88, 143.71, 129.27, 127.07, 119.65, 94.83, 73.02, 71.29, 51.70, 46.27, 45.67, 44.26, 43.62, 38.49, 38.30, 37.92, 37.53, 35.54, 34.64, 30.98, 28.97, 27.57, 22.93, 21.87, 21.73, 18.87, 14.55.

Example 6

Acyl Group Hydrolysis at C-3

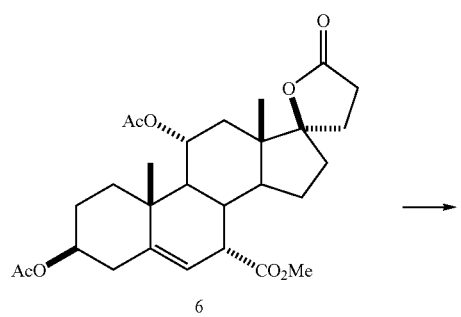

A solution of the diacetylester 6 (5.01 g) in 0.15N potassium carbonate in methanol (50 ml) is stirred at room temperature and the reaction monitored by TLC. When the starting material 6 is no longer detected the mixture is diluted with water (200 ml) and extracted with ethyl acetate (3×200 ml). The combined extracts are washed with water (100 ml), brine (100 ml), dried over magnesium sulfate and concentrated at reduced pressure to dryness. The residue is chromatographed over silica gel with ethyl acetate/hexane to give the 3-hydroxy compound 7. $^{13}$C NMR (CDCl$_3$) δ 176.29, 173.18, 169.96, 144.88, 118.56, 94.93, 71.32, 70.93, 60.34, 51.63, 49.87, 44.61, 43.77, 42.49, 38.24, 37.79, 35.50, 34.72, 31.34, 30.94, 28.97, 22.92, 21.73, 18.94, 14.53.

Example 7

Oxidation of 3-hydroxysteroids

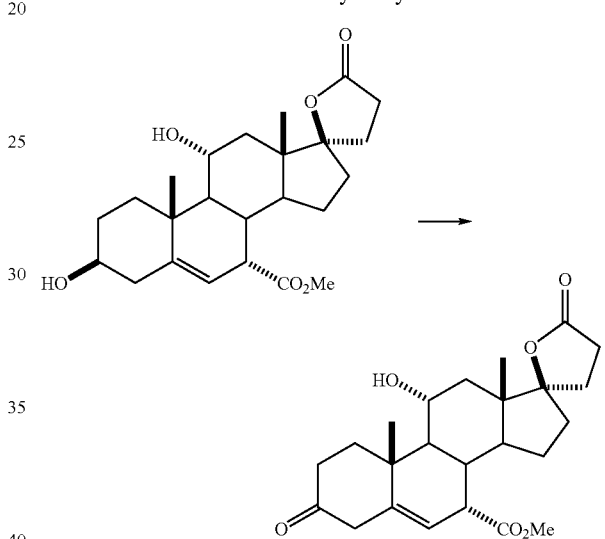

A solution of the diol (300 mg, 0.72 mmol), 14 mg of KBr, 130 mg of NaHCO$_3$, 4 mg of TEMPO in 6 mL of CH$_2$Cl$_2$ and 2 mLH$_2$O was cooled to 18° C. and slowly treated with 0.73 mL (1.1 M) NaOCl. When TLC showed the reaction complete the NaHSO$_3$ was added to quench excess hypochlorite. The product was isolated with EtOAc and and crystallized from EtOAc to give 230 mg of the deconjugated enone. $^{13}$C NMR (CDCl$_3$) δ 209.16, 176.57, 172.72, 143.25, 119.13, 95.45, 68.50, 51.69, 49.10, 49.0, 46.94, 46.05, 43.68, 42.66, 42.13, 38.33, 37.54, 35.46, 34.51, 22.84, 18.18, 15.09. Upon standing in EtOAc solution the double bond slowly isomerized to the conjugated position.

Example 8

Preparation of Tricarbonates

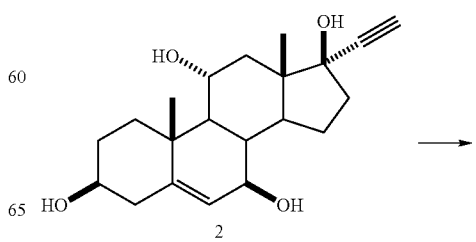

-continued

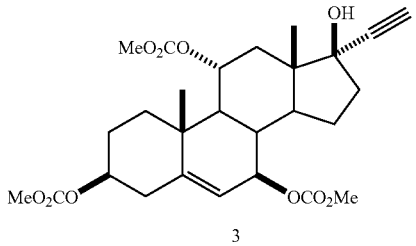

3

A solution of 9.97 g of the tetrol 2 in 80 mL of pyridine and 15 mL of triethylamine is treated with 33.6 g of N-methoxycarbonyloxybenztriazole and 360 mg of DMAP at room temperature overnight. The mixture is diluted with water (150 ml) and the resultant precipitate filtered and dried. Recrystalization from ethyl acetate—methanol gives the tricarbonate 3. TLC (100% EtOAc) rf=0.94

Example 9

Hydroformylation of Tricarbonates

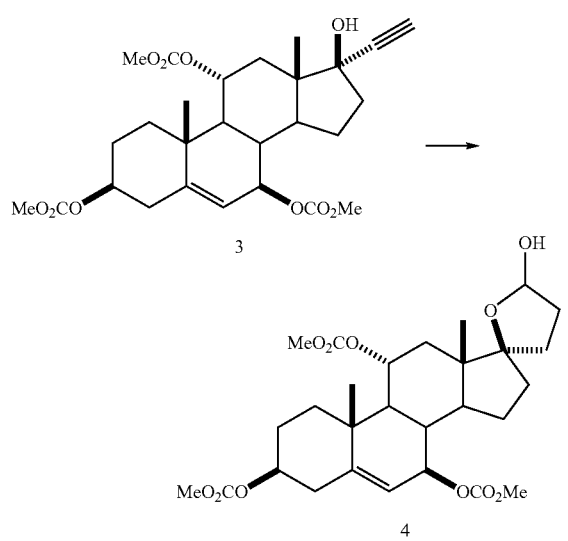

A solution of 9.95 g of 3, 18 mg of $Rh_2(OAc)_2$ and 430 mg of triphenylphosphine in 100 mL of ethyl acetate is pressurized to 190 psi with carbon monoxide/hydrogen (1:1) and heated at 80° C. overnight. The reaction mixture is filtered while still warm. On cooling, the product 4 crystallizes and is collected by filtration. TLC (75% EtOAc/Hex) rf=0.96

Example 10

Carbonylation of tri-carbonates

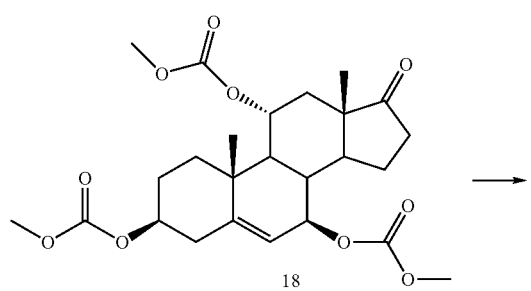

18

-continued

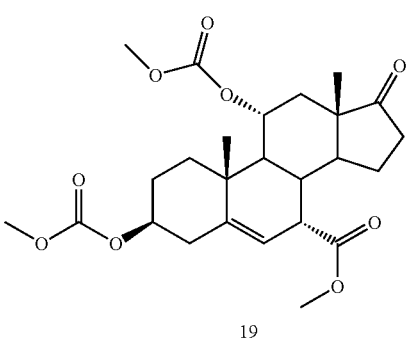

19

A mixture of tricarbonate 18 (20.00 g), di-isopropylethylamine (7.1 ml), Pd(dppp)Br$_2$ (582 mg)in MeOH (300 ml) is pressurized with CO (1200 psi) and heated at 70° C. for 18 hours. The cooled reaction mixture is filtered through magnesol and concentrated. The residue is dissolved in ethyl acetate and washed with water (2x), dried over MgSO$_4$, filtered, and concentrated. The residue is recrystallized from methanol to give 19. $^{13}$C NMR (CDCl$_3$) δ 217.64, 172.86, 155.35, 155.04, 143.86, 120.19, 77.26, 79.87, 55.14, 54.89, 52.25, 47.68, 47.26, 46.17, 43.69, 38.8838.67, 37.75, 37.57, 36.02, 34.01, 27.85, 22.06, 19.32, 13.87.

Example 11

Carbonylation of di-carbonates

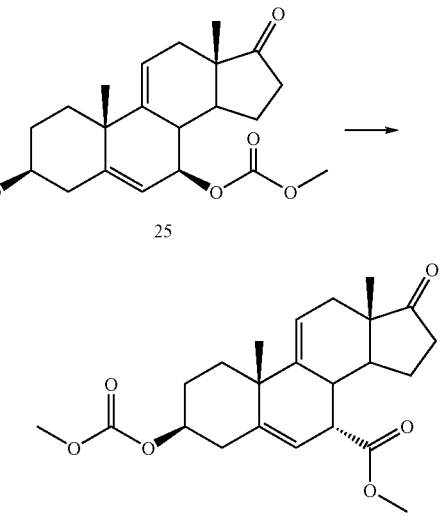

The dicarbonate 25 (521 mg, 1.25 mmol) diisopropylamine (0.219 ml, 1.25 mmol), Br$_2$Pd(PPh$_3$)$_2$ (18 mg, 0.063 mmol) and NaBr (26 mg, 0.25 mmol) in EtOH (10 ml) were heated at 80° C. under 1300 psi carbon monoxide for 12 hrs. The cooled reaction mixture was concentrated and chromatographed using 50/50 EtOAc/Hexane and 100 g silica to give the ester 14. $^{13}$C NMR (CDCl$_3$) δ 221.27,172.47, 155.44, 143.94, 142.47, 119.68, 118.67, 77.96, 54.98, 46.91, 45.55, 44.98, 39.30, 38.36, 37.41, 37.79, 36.60, 34.71, 33.59, 28.14, 22.97, 13.94.

Example 12

Preparation of di-carbonates

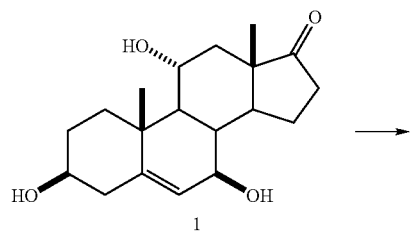

A solution of the triol 1 (2.0 g) in 5 mL of pyridine is cooled to 0° C. and treated with a solution of methyl chloroformate (3.4 mL) in 5 mL of $CH_2Cl_2$. The mixture is slowly warmed to rt and then 50 ml each of water and $CH_2Cl_2$ are added. The phases are separated and the aqueous phase extracted with 3×20 mL of $CH_2Cl_2$. The combined organic layers are washed with 20 mL of water and concentrated. Silica gel chromatography with 50% EtOAc/Hex afforded the dicarbonate 12. $^{13}C$ NMR ($CDCl_3$) δ 221.37, 155.46, 143.94, 142.48, 119.68, 118.67, 77.97, 60.91, 54.98, 46.92, 45.56, 38.36, 39.30, 37.41, 34.72, 33.59, 28.14, 22.97, 14.66, 13.95.

Example 13

Hydrolysis of Carbonates

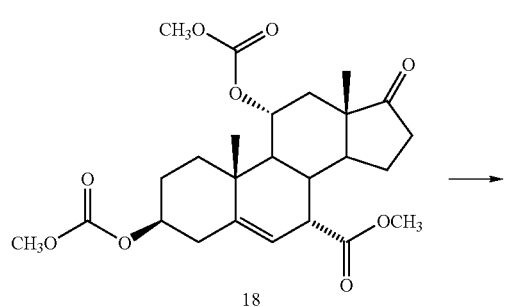

The dicarbonate 18 (0.86 g) and potassium carbonate (1.49 g) in MeOH (10 mL) is stirred at room temperature for 12 hr. The reaction mixture is diluted with ethyl acetate (50 ml), washed with water (2×50 ml), dried over $MgSO_4$ and concentrated to a clear colorless oil. Hydrolysis results in isomerization of the C7 ester. The carbonate is further purified by column chromatography over silica gel eluting with 30% acetone/$CH_2Cl_2$ to obtain 19 as a mixture of α and β isomers at C7. HPLC: Phenomenex Nucleosil C18, 65:35 ACN:$H_2O$, t=4.17 min, t=4.60 min.

Example 14

Oxidation of 3-hydroxy-$\Delta^5$-enes

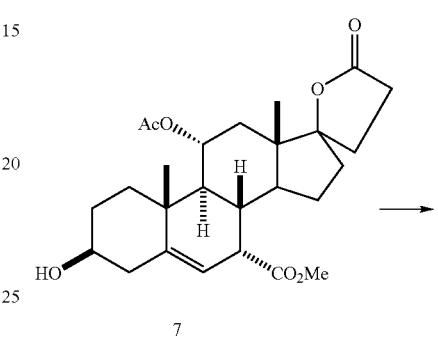

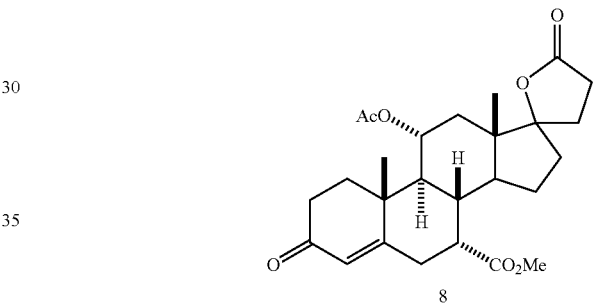

A mixture of alcohol 7 (6.0 g), $CH_2Cl_2$ (40 mL), water (9.0 mL), 2,2,6,6-tetramethylpiperidine-1-oxyl (TEMPO) (38 mg), KBr (142 mg) and sodium bicarbonate (4.0 g) is cooled to 5° C. To this mixture is slowly added 14.1 ml of 1.1 M NaOCl. After the addition the mixture is allowed to stir for an additional 1 h and acidified with dilute HCl. The product is isolated with $CH_2Cl_2$. $^{13}C$ NMR ($CDCl_3$) δ 198.83, 175.95, 169.63, 168.87, 159.04, 130.89, 94.52, 74.0, 70.99, 52.00, 46.95, 46.21, 44.59, 44.49, 38.65, 38.41, 37.95, 35.31, 33.97, 32.05, 30.95, 28.91, 22.57, 21.72, 21.16, 20.07, 14.97.

Example 15

Dehydration of 11-hydroxy Intermediates

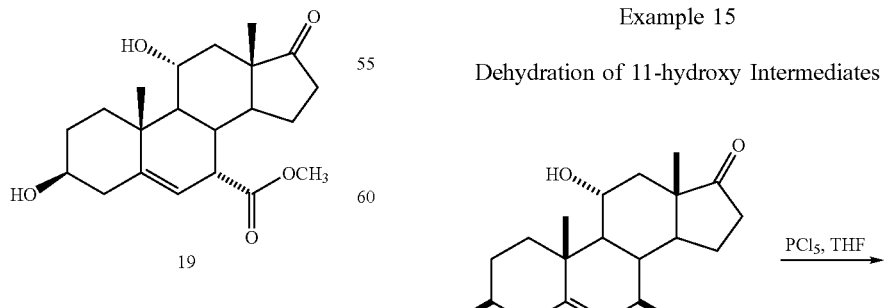

-continued

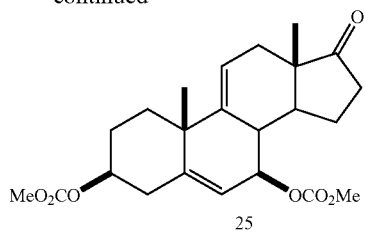
25

PCl$_5$ (1.08 g) was added to a solution of the alcohol in THF at −51° C. which resulted in a temperature rise to −48° C. After 2 hrs the mixture was poured into aqueous NaHCO$_3$ and extracted with EtOAc and concentrated. The material was chromatographed on silica gel with EtOAc/hexane to afford the diene 25. $^{13}$C NMR (CDCl$_3$) δ 220.52, 155.39, 154.92, 142.57, 141.92, 122.07, 120.02, 80.26, 54.85, 54.58, 47.58, 46.53, 39.50, 38.5, 37.34, 36.21, 33.13, 26.0, 26.78, 24.26, 13.75.

Example 16

Bioconversion of 3β-hydroxyandrosta-5,9(11)-dien-17-one to 3β,7β-dihydroxyandrosta-5,9(11)-dien-17-one The bioconversion of 3β-hydroxyandrosta-5,9(11)-dien-17-one (I) to 3β,7β-dihydroxyandrosta-5,9(11)-dien-17-one is performed using a submerged culture of *Diplodia gossypina* ATCC 20571 (synonym *Botryodiplodia theobromae* IFO 6469) at a 10-L fermentation scale.

(A) Primary-Seed Stage

Frozen vegetative cells of *Diplodia gossypina* (ATCC 20571) are thawed, transferred to potato-dextrose-agar plates (PDA), and incubated at 28° for 72 hours. Single mycelial-plugs (6–7 mm diameter) are used to inoculate siliconized stippled shake flasks (500 mL) containing 100 mL primary-seed medium. Primary-seed medium consists of (per liter): dextrin, 50 g; soy flour, 35 g; cerelose, 5 g; cobalt chloride hexahydrate, 2 mg; silicone defoamer (SAG 471), 0.5 mL. The pre-sterilization pH is adjusted to 7.0–7.2 with sodium hydroxide (2N). The fermentation medium is sterilized, inoculated with *Diplodia gossypina* ATCC 20571 and incubated for 48 hours at 28°, using a controlled-environment incubator-shaker set at 280 rpm. (1" orbital stroke).

(B) Secondary-Seed Stage

Ten-liter secondary-seed fermentations are inoculated using vegetative primary-seed culture (1.2 mL; 0.012% (v/v) inoculation rate). Secondary-seed medium contains (per liter of RO water): cerelose, 60 g; soy flour, 25 g; soybean oil, 30 mL; magnesium heptahydrate, 1 g; potassium dihydrogen phosphate, 0.74 g; polyoxyethylenesorbitan monooleate, 2 mL; silicone defoamer (SAG 471), 0.5 mL. The pre-sterilization pH is adjusted to 3.95–4.00 with concentrated sulfuric acid. The fermentors, containing secondary-seed medium, are sterilized for 20 minutes at 121° using both jacket and injection steam. The agitation rate during sterilization is 200 RPM. Post-sterilization, the medium pH is adjusted to 4.0 using sterile sulfuric acid (5%). *Diplodia gossypina* ATCC 20571 is incubated at 28° using the following initial parameters: agitation, 100 RPM; back pressure=5 psig; airflow=2.5 SLM (0.25 VVM); low DO set-point, 30%; pH control, none. When the DO first drops to 30%, the airflow is increased to 5 SLM (0.5 VVM). When the culture reaches low DO again, 30% DO is maintained using agitation control. Secondary-seed cultures are harvested at approximately 60 hours post-inoculation, when the OUR is between about 10 and about 15 mM/L/h.

(C) Steroid Bioconversion

Ten-liter steroid-bioconversion cultures are prepared. At about 24 hours post-inoculation, 120 g micronized 3β-hydroxyandrosta-5,9(11)-dien-17-one, slurried in a minimal volume of polyoxyethylenesorbitan monooleate (0.2%), is added to the 10-L fermentation.

Bioconversion cultures are assayed on a daily basis for 3β,7β-hydroxyandrosta5,9(11)-dien-17-one. Bioconversion of 3β-hydroxyandrosta-5,9(11)-dien-17-one to 3β,7β-hydroxyandrosta-5,9( 11)-dien-17-one is complete approximately 3 days post-inoculation.

Example 17

Bioconversion of 5-androsten-3β-ol-17-one to 5-androsten-3β,7β,11α-triol-17-one

The bioconversion of 5-androsten-3β-ol-17-one to 5-androsten-3β,7β,11α-triol-17-one is performed using a submerged culture of *Absidia coerulea* ATCC 6647 (synonym *Absidia orchidis*) at a 10-L fermentation scale.

(A) Primary-Seed Stage

Primary-seed cultures of *Absidia coerulea* ATCC 6647 are prepared as described for *Diplodia gossypina* ATCC 20571 in EXAMPLE 16.

(B) Secondary-Seed Stage

Ten-liter secondary-seed fermentations are inoculated using 1.2 mL vegetative primary-seed culture (0.012% [v/v] inoculation rate). Secondary-seed medium contains (per liter of RO water): dextrin, 50 g; soyflour, 35 g; cerelose, 5 g; cobalt chloride hexahydrate, 2 mg; silicone defoamer (SAG 471), 0.5 mL; pre-sterilization pH 4.95–5.00, adjusted with concentrated sulfuric acid. The fermentors, containing secondary-seed medium, are sterilized for 20 minutes at 121° using both jacket and injection steam. The agitation rate during sterilization is 200 r.p.m. Post-sterilization, the medium pH is adjusted to 5.0 using sterile sulfuric acid (5%). *Absidia coerulea* ATCC 6647 is incubated at 28° using the following initial parameters: agitation, 100 r.p.m.; back pressure=5 psig; airflow=2.5 SLM (0.25 VVM); low DO set-point, 50%; pH control, none. When the DO first drops to 30%, the airflow is increased to 5 SLM (0.5 VVM). When the culture reaches low DO again, 30% DO is maintained using agitation control. Secondary-seed cultures are harvested about 76 hours post-inoculation, when the OUR is between about 4 and about 7 mM/L/h.

(C) Steroid Bioconversion

Ten-liter steroid-bioconversion fermentations are inoculated using 500 mL vegetative secondary-seed culture (5% [v/v] inoculation rate). Steroid-bioconversion medium contains (per liter of RO water): dextrin, 50 g; soyflour, 35 g; cerelose, 20 g; silicone defoamer (SAG 471), 0.5 mL; pre-sterilization pH 2.95–3.00, adjusted with concentrated sulfuric acid. Sterilization conditions are as described for secondary-seed medium. Post-sterilization, the medium pH is adjusted to 3.0 using sterile sulfuric acid (5%). *Absidia coerulea* ATCC 6647 is incubated at 28° using the same initial parameters as those used for secondary-seed cultivation. At about 17 hours post-inoculation, 200 g micronized 5-androsten-3β-ol-17-one, slurried in a minimal volume of 0.2% octylphenoxypolyethoxyethanol, is added to the 10-L fermentation.

Bioconversion cultures are assayed on a daily basis for 5-androsten-3β,7β,11α-triol-17-one using TLC. One milliliter of whole beer is extracted with 10 mL methanol. Cells are separated from the aqueous-methanol mixture by centrifugation (3,000×g for 10 minutes), and several microliters applied to a TLC plate. The TLC plate is developed in cyclohexane:ethyl acetate:methanol (90:60:15) and the product visualized by spraying the TLC with 50% sulfuric acid, followed by charring in an oven. Product is compared with authentic standard, which turns blue on spraying with 50% sulfuric acid. Bioconversion of 5-androsten-3β-ol-17-one to 5-androsten-3β,7β-diol-17-one is complete approximately 4 days post-inoculation.

Bioconversion of 5-androsten-3β-ol-17-one to 5-androsten-3β,7β,11α-triol-17-one is complete approximately 6–7 days post-inoculation.

(D) Isolation Procedure

The whole beer solids are recovered by centrifugation. The liquid is discarded. The rich solids are extracted using 10 liters of 85% acetone 15% water at 45° C. to 50° C. and the warm extract is clarified by filtration. The rich filtrate is concentrated by distillation to remove acetone generating an aqueous slurry of crude crystals. The crystal slurry is filtered and the mother liquor is discarded. The water-wet crystals are triturated in 600 milliliters of methylene chloride to remove impurities, dissolved in 700 milliliters of methanol (by heating to 55° C.), and then decolorized with 5 grams of Darco G-60 carbon. After filtration to remove carbon, the filtrate is concentrated to crystallize the product. The methanol is removed further by adding 300 mL of n-butyl acetate and concentrating to a thick crystal slurry. The crystals are filtered, washed with n-butyl acetate, and dried to give 75.5 grams of crude crystalline 5-androsten-3β,7β,11α-triol-17-one.

The crude crystals are triturated in 600 milliliters of methylene chloride to remove additional impurities, dissolved in 700 milliliters of methanol (by heating to 55° C.), and then decolorized with 5 grams of Darco G-60 carbon. After filtration to remove carbon, the filtrate is concentrated to crystallize the product. The methanol is removed further by adding 300 mL of n-butyl acetate and concentrating to a thick crystal slurry. The crystals are filtered, washed with n-butyl acetate, and dried to give 42.1 grams of purified crystalline 5-androsten-3β,7β,11α-triol-17-one.

What is claimed is:
1. A compound of Formula I:

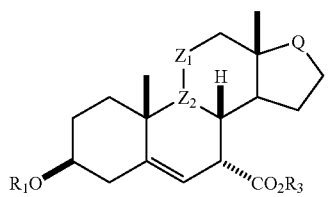

Formula I wherein:
a) $R_1$ is selected from H or $COR_4$;
   $R_4$ is $C_1$–$C_6$ alkyl or $C_1$–$C_6$ alkoxy;
   $R_3$ is $C_1$–$C_6$ alkyl;
   $Z_1$ is

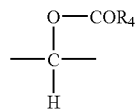

wherein O—$COR_4$ is in the α configuration;
$Z_2$ is —CH—;
or $Z_1$ and $Z_2$ may be taken together to form a double bond;
Q is

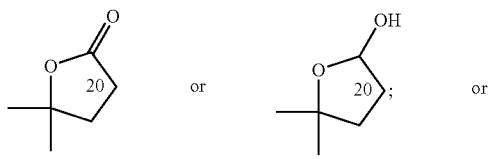

b) $R_1$ is $COR_4$;
   $R_4$ is $C_1$–$C_6$ alkyl or $C_1$–$C_6$ alkoxy;
   $R_3$ is $C_1$–$C_6$ alkyl;
   $Z_1$ is —$CH_2$— or

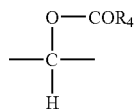

wherein O—$COR_4$ is in the α configuration;
$Z_2$ is —CH—;
or $Z_1$ and $Z_2$ may be taken together to form a double bond; and
Q is

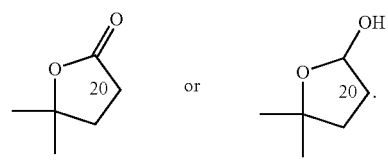

2. The compound of claim 1, wherein $R_1$ is H;
$R_4$ is $C_1$–$C_6$ alkyl or $C_1$–$C_6$ alkoxy;
$R_3$ is $C_1$–$C_6$ alkyl;
$Z_1$ is

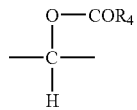

wherein O—$COR_4$ is in the α configuration;
$Z_2$ is —CH—;
or $Z_1$ and $Z_2$ may be taken together to form a double bond.

3. A process for the preparation of 7-carboxy substituted steroids of Formula I

Formula I

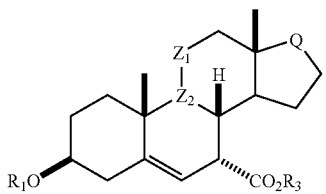

wherein $R_1$ is independently selected from H or $C(O)R_4$;
$R_4$ is $C_1$–$C_6$ alkyl or $C_1$–$C_6$ alkoxy;
$R_3$ is $C_1$–$C_6$ alkyl;
$Z_1$ is —$CH_2$— or

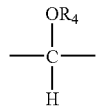

wherein $OR_4$ is in the α configuration;
$Z_2$ is —CH—;
or $Z_1$ and $Z_2$ may be taken together to form a double bond;

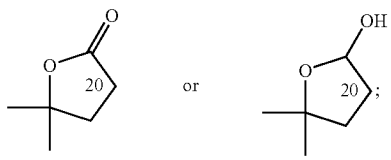

Q is
comprising reacting a steroid intermediate of Formula II,

Formula II

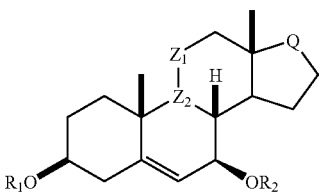

wherein $R_1$ and $R_2$ are independently selected from H or $C(O)R_4$;
$Z_1$, $Z_2$ and Q are as for Formula I;
with carbon monoxide in the presence of an alcohol, an amine, and a palladium catalyst.

4. The process of claim 3, wherein the alcohol is $C_1$–$C_6$ alkyl-OH or benzyl alcohol.

5. The process of claim 4, wherein the alcohol is selected from methanol, ethanol, propanol, butanol, 2-butanol, isopropanol, or benzyl alcohol.

6. The process of claim 5, wherein the alcohol is methanol, propanol, butanol, or ethanol.

7. The process of claim 6, wherein the alcohol is methanol.

8. The process of claim 3, wherein the pressure of carbon monoxide is between about 500 psi to about 2000 psi.

9. The process of claim 8, wherein the pressure of carbon monoxide is between about 800 psi to about 1500 psi.

10. The process of claim 9, wherein the pressure of the carbon monoxide is between about 1200 psi to about 1400 psi.

11. The process of claim 3, wherein the palladium catalyst is selected from palladium acetate, palladium (II) acetylacetonate, palladium (0)bis(dibenzylideneacetone)($Pd_2(dba)_3$), palladium 1,3-diphenylphosphinopropane dibromide, ($Pd(dppp)Br_2$), dimethyl-2-(dimethylphosphino)ethylphosphine palladium or bistriphenylphosphine palladium dibromide ($Pd_2(Ph_3P)_2Br_2$).

12. The process of claim 11, wherein the palladium catalyst is selected from palladium bromide, $Pd_2(dba)_3$, $Br_2Pd(PPh_3)_2$, (dppe)$PdBr_2$, or $Pd(OAc)_2$.

13. The process of claim 12, wherein the palladium catalyst is $Br_2Pd(PPh_3)_2$.

14. The process of claim 12, wherein the palladium catalyst is $Pd_2(dba)_3$.

15. The process of claim 3, wherein the amine is a tertiary amine.

16. The process of claim 15, wherein the base is selected from N-methylmorpholine, triethylamine, and diisopropylethylamine.

17. The process of claim 3, wherein the reaction is conducted at a temperature between about 20° C. to about 150° C.

18. The process of claim 17, wherein the reaction is conducted at a temperature between about 70° C. to about 80° C.

19. The process according to claim 3 further comprising the steps:
a) reacting a 17-keto steroid of Formula III Formula III

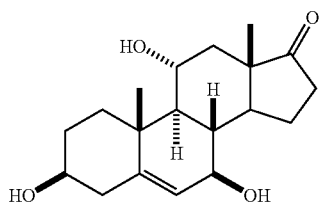

with trimethylsilyl chloride, hexamethyldisilazane in the presence of saccharin to form a silylated 17-keto steroid;
b) reacting the silylated 17-keto steroid formed in step a) with acetylene in the presence of a suitable base;
b) reacting the silylated 17-keto steroid formed in step a) with acetylene in the presence of a suitable base;
c) isolating the product of step b) in the presence of acid or fluoride ion to give an 17-acetylenic alcohol of Formula IV:

Formula IV

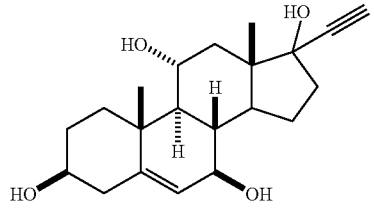

20. The process of claim 19 further comprising reacting the 17-acetylenic tri-alcohol of formula IV with an acylating reagent in the presence of a base to give a triacyl compound of Formula V:

Formula V

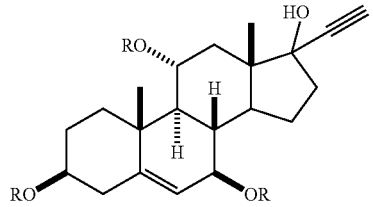

wherein R is $C_1$–$C_4$ alkyl-CO—, $C_1$–$C_4$ alkyl-OCO— or phenyl-$CH_2$O—CO—.

21. The process of claim 20 further comprising: reacting a triacyl compound of Formula V with carbon monoxide in the presence of a rhodium catalyst and hydrogen and carbon monoxide to give a 17-lactol of Formula VI, wherein R is $C_1$–$C_4$ alkyl-CO—, $C_1$–$C_4$ alkyl-OCO— or phenyl-$CH_2$O—CO—:

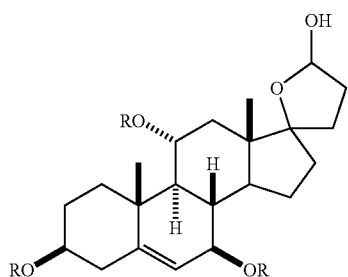

Formula VI

22. The process of claim 21 further comprising oxidizing the lactol of Formula VI to the lactone of Formula VII, wherein R is $C_1$–$C_4$ alkyl-CO—, $C_1$–$C_4$ alkyl-OCO— or phenyl-$CH_2$O—CO—:

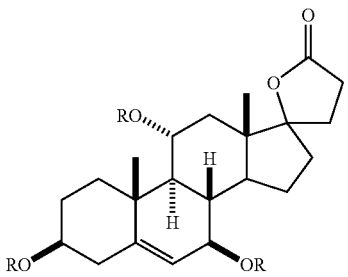

Formula VII

23. The process of claim 22 further comprising reacting a lactone of Formula VII with carbon monoxide in the presence of methanol, a tertiary organic base and a palladium catalyst at a pressure of from 500 psi to 1500 psi and a temperature of from 25° C. to 150° C. to give an ester diacyl compound of Formula VIII, wherein R is $C_1$–$C_4$ alkyl-CO—, $C_1$–$C_4$ alkyl-OCO— or phenyl-$CH_2$O—CO—:

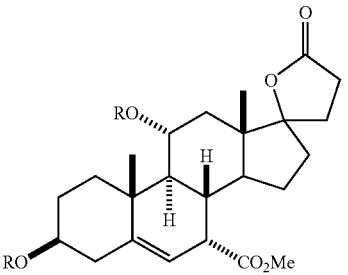

Formula VIII

24. The process of claim 23 further comprising hydrolyzing an acyl compound of Formula VIII in the presence of methanol or an aqueous solvent and a base to give a 3-alcohol of Formula IX, wherein R is $C_1$–$C_4$ alkyl-CO—, $C_1$–$C_4$ alkyl-OCO— or phenyl-$CH_2$O—CO—:

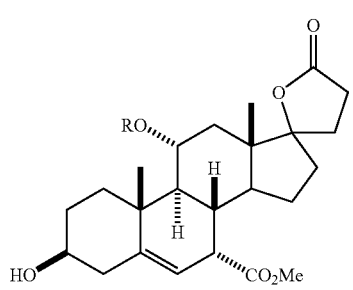

Formula IX

25. The process of claim 3, further comprising using the compound of formula I to produce eplerenone comprising oxidizing an alcohol of Formula IX to give a ketone of Formula X, wherein R is $C_1$–$C_4$ alkyl-CO—, $C_1$–$C_4$ alkyl-OCO— or phenyl-$CH_2$O—CO—:

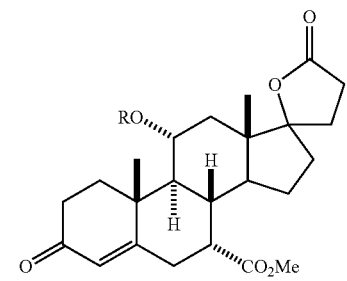

Formula X

26. The process of claim 25 further comprising hydrolyzing the 11-acyl group of a compound of Formula X with methanol in the presence of a base to give an 11-hydroxy compound of Formula XI:

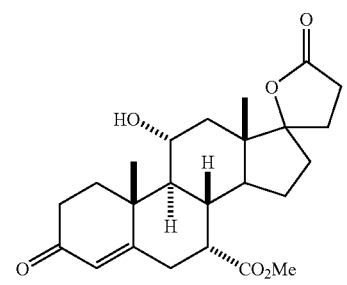

Formula XI

27. The process of claim 26 further comprising reacting an 11-hydroxy compound of Formula XI with phosphorus pentachloride to give a dieneone of Formula XII:

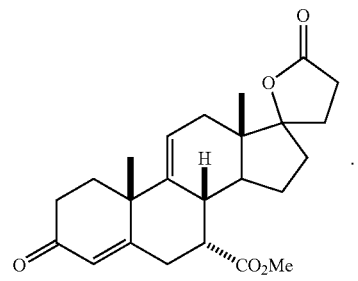

Formula XII

28. The process of claim 27 further comprising oxidizing a dieneone of Formula XII to form Eplerenone

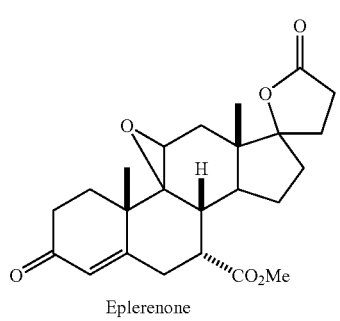

Formula XIII

Eplerenone

29. A process comprising reacting an acetylenic compound of Formula XVIII:

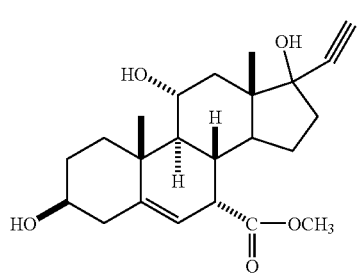

Formula XVIII with carbon monoxide and hydrogen in the presence of a rhodium catalyst and a tertiary organic base to give a lactol of Formula XIX wherein R is H:

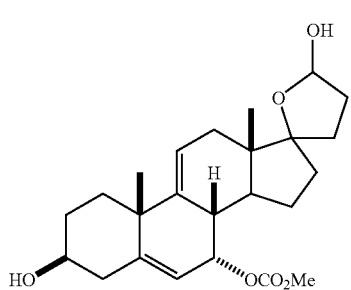

Formula XIX

30. The process of claim 29 further comprising oxidation of a lactol of Formula XIX to give a lactone of Formula XII:

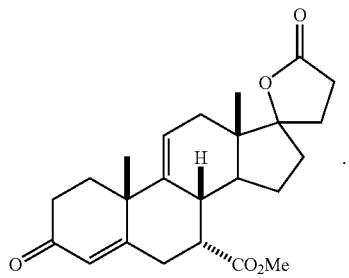

Formula XII

31. The process of claim 30 further comprising oxidizing a compound of Formula XII to give Formula XIII, eplerenone:

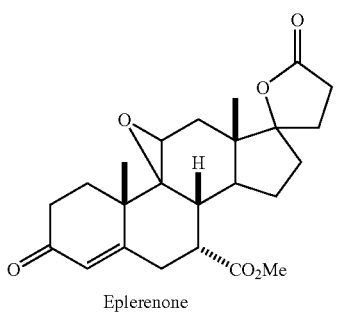

Formula XIII

Eplerenone

32. A process for preparing eplerenone comprising the steps:

a) reacting a keto steroid of Formula III with acetic anhydride in the presence of a tertiary organic base to give a triacetate of Formula XX:

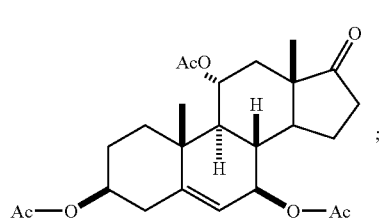

Formula XX b) reacting a di-acyl compound of Formula XVIII with carbon monoxide in the presence of a palladium catalyst, methanol and a tertiary organic base at a pressure of from 250 psi to 1500 psi and a temperature of from 25° C. to 150° C. to give a compound of Formula XXI:

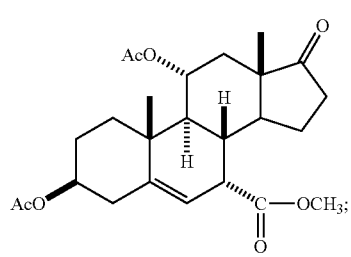

Formula XXI c) hydrolyzing a diacetate of Formula XXI to give the dihydroxy compound of Formula XXII:

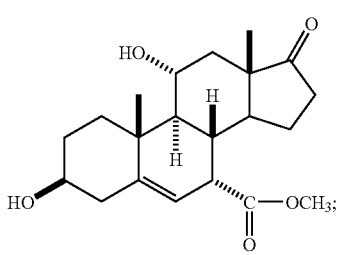

Formula XXII d) reacting a compound of Formula XXII with acetylene in the presence of a strong base to give an acetylenic compound of Formula XXIII:

Formula XXIII

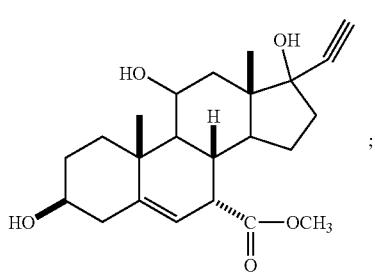

e) reacting an acetylenic compound of Formula XXI with carbon monoxide and hydrogen in the presence of a rhodium catalyst and a tertiary organic base to give a lactol of Formula XXIV:

Formula XXIV

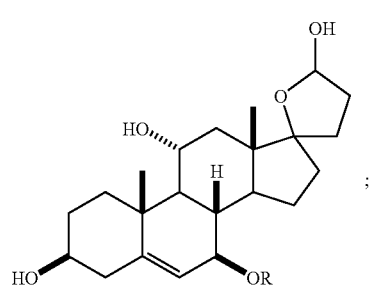

f) oxidation of a lactol of Formula XXII, wherein R is H, to give a lactone of Formula XI:

Formula XI

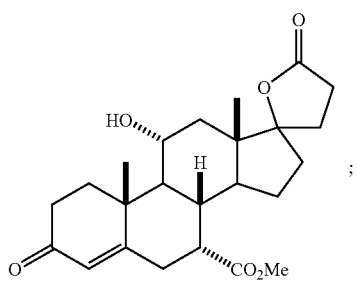

g) dehydrating a compound of Formula XII to give the compound of Formula XII:

Formula XII

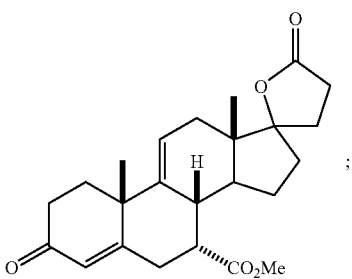

h) oxidizing a dieneone of Formula XII whereby Eplerenone (Formula XIII) is obtained:

Formula XIII

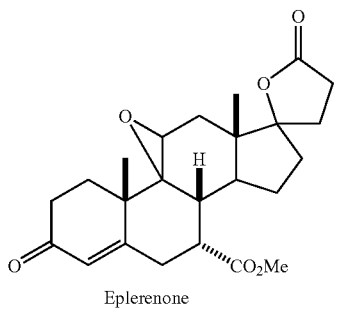

Eplerenone

33. A process for preparing eplerenone comprising the steps:
a) reacting a diol of Formula XXV Formula XXV

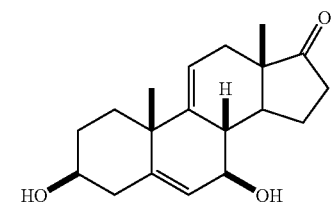

with an $C_{1-6}$ alkylchloroformate in the presence of a tertiary organic base to give a dicarbonate of Formula XXVI:

Formula XXVI

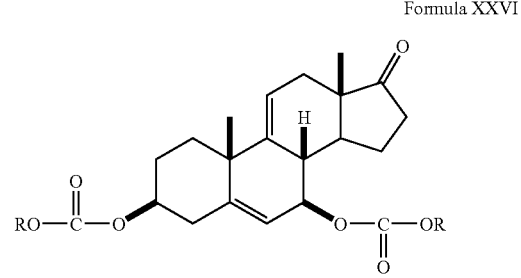

wherein R is $C_{1-6}$ alkyl;

b) reacting a di-acyl compound of Formula XXVI with carbon monoxide in the presence of a palladium catalyst, methanol and a tertiary organic base at a pressure of from 250 psi to 1500 psi and a temperature of from 25° C. to 150° C. to give a compound of Formula XVII:

Formula XVII

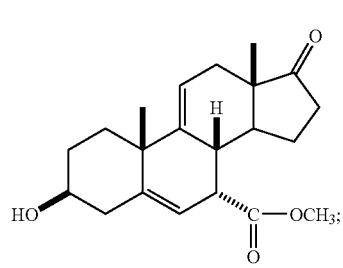

c) reacting a compound of Formula XVII with acetylene in the presence of a strong base to give an acetylenic compound of Formula XVIII;

Formula XVIII

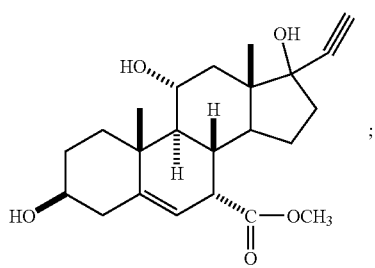

d) reacting an acetylenic compound of Formula XVIII with carbon monoxide and hydrogen in the presence of a rhodium catalyst and a tertiary organic base to give a lactol of Formula XIX wherein R is H:

Formula XIX

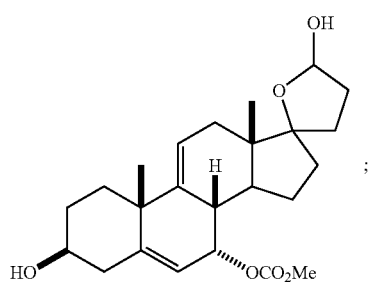

e) oxidation of a lactol of Formula XIX to give a lactone of Formula XII:

Formula XII

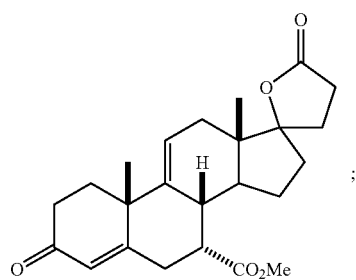

f) oxidation of a compound of Formula XII to give Formula XIII, eplerenone:

Formula XIII

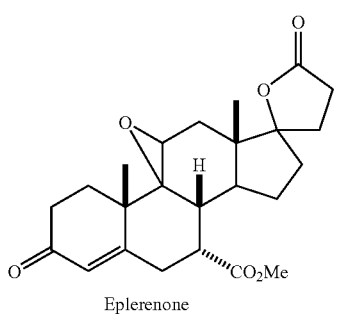

Eplerenone

* * * * *